United States Patent [19]
Gajda et al.

[11] Patent Number: 5,434,326
[45] Date of Patent: * Jul. 18, 1995

[54] DISCRETE MOLECULAR SIEVE AND USE IN AROMATIC-OLEFIN ALKYLATION

[75] Inventors: Gregory J. Gajda, Mount Prospect, Ill.; Robert L. Patton, Katonah, N.Y.; Stephen T. Wilson, Libertyville, Ill.

[73] Assignee: UOP, Des Plaines, Ill.

[*] Notice: The portion of the term of this patent subsequent to Jan. 4, 2011 has been disclaimed.

[21] Appl. No.: 176,140

[22] Filed: Dec. 30, 1993

Related U.S. Application Data

[60] Continuation-in-part of Ser. No. 18,121, Feb. 16, 1993, Pat. No. 5,276,236, which is a division of Ser. No. 814,749, Dec. 26, 1991, Pat. No. 5,240,891.

[51] Int. Cl.[6] .............................. C07C 2/66
[52] U.S. Cl. ........................ 585/467; 585/446; 585/458; 585/466; 585/475
[58] Field of Search .......... 585/446, 458, 466, 467, 585/475

[56] References Cited

U.S. PATENT DOCUMENTS

| | | | |
|---|---|---|---|
| 3,751,504 | 8/1973 | Keown et al. | 260/672 T |
| 4,034,053 | 7/1977 | Kaeding et al. | 260/672 T |
| 4,440,871 | 4/1984 | Lok et al. | 502/214 |
| 4,567,029 | 1/1986 | Wilson et al. | 423/306 |
| 4,721,827 | 1/1988 | Cullo et al. | 585/467 |
| 4,758,419 | 7/1988 | Lok et al. | 423/306 |
| 4,793,984 | 12/1988 | Lok et al. | 423/329 |
| 4,882,038 | 11/1989 | Lok et al. | 208/111 |

*Primary Examiner*—P. Achutamurthy
*Attorney, Agent, or Firm*—Thomas K. McBride; John F. Spears, Jr.; Richard E. Conser

[57] ABSTRACT

This invention presents a novel MgAPSO molecular sieve, containing a critical range of magnesium in the sieve framework and having a small crystallite size, which is particularly active for hydrocarbon conversion. The sieve advantageously is incorporated, along with a refractory inorganic oxide, into a catalyst formulation which is useful for alkylation. When utilized in a process for alkylating an aromatic with an olefin, for example in the production of cumene or ethylbenzene, the sieve catalyst shows favorable selectivity.

19 Claims, 2 Drawing Sheets

DISCRETE MOLECULAR SIEVE AND USE IN AROMATIC-OLEFIN ALKYLATION

CROSS-REFERENCE TO RELATED APPLICATIONS

This application is a continuation-in-part of prior application Ser. No. 08/018,121, filed Feb. 16, 1993, now U.S. Pat. No. 5,276,236, which is a division of Ser. No. 07/814,749, filed Dec. 26, 1991, now U.S. Pat. No. 5,240,891, both of which are incorporated by reference.

FIELD OF THE INVENTION

This invention relates to an improved molecular sieve and its use for the conversion of hydrocarbons. More specifically, the invention concerns a magnesium-containing non-zeolitic molecular sieve which has a narrowly defined composition and is particularly useful for alkylation of aromatics and olefins.

GENERAL BACKGROUND AND RELATED ART

A large variety of molecular sieves have been disclosed in the art as useful in catalysts for hydrocarbon conversion. The most well known are the crystalline aluminosilicate zeolites formed from corner-sharing $AlO_2$ and $SiO_2$ tetrahedra. The zeolites generally feature pore openings of uniform dimensions, significant ion-exchange capacity and the capability of reversibly desorbing an adsorbed phase which is dispersed throughout the internal voids of the crystal without displacing any atoms which make up the permanent crystal structure. Zeolites often are characterized by a critical, usually minimum, silica/alumina ratio.

More recently, a class of useful non-zeolitic molecular sieves containing framework tetrahedral units ($TO_2$) of aluminum ($AlO_2$), phosphorus ($PO_2$) and at least one additional element EL ($ELO_2$) has been disclosed as being useful in hydrocarbon conversion. "Non-zeolitic molecular sieves" include the "ELAPSO" molecular sieves as disclosed in U.S. Pat. No. 4,793,984 (Lok et al.), "SAPO" molecular sieves of U.S. Pat. No. 4,440,871 (Lok et al.) and crystalline metal aluminophosphates—MeAPOs where "Me" is at least one of Mg, Mn, Co and Zn—as disclosed in U.S. Pat. No. 4,567,029 (Wilson et al). Framework As, Be, B, Cr, Fe, Ga, Ge, Li, Ti or V and binary metal aluminophosphates are disclosed in various species patents. Particularly relevant to the present catalyst is U.S. Pat. No. 4,758,419 (Lok et al.), which discloses MgAPSO non-zeolitic molecular sieves. Generally the above patents teach a wide range of framework metal concentrations, e.g., the mole fraction of (magnesium+silicon) in Lok et al. '419 may be between 0.02 and 0.98 with a preferable upper limit of 0.35 mole fraction and magnesium concentration of at least 0.01, for sieves useful in hydrocarbon conversion.

The catalytic alkylation of aromatics with olefins is practiced commercially to yield such petrochemical intermediates as ethylbenzene, cumene, and linear alkylbenzenes. Such monoalkylaromatic compounds are important chemical precursors in the production of resins, surface-active agents, and other products. Polyalkylaromatic compounds such as diethylbenzene and diisopropylbenzene are lower-volume commercial products.

Known aromatic-olefin alkylation catalysts include Friedel-Crafts catalysts in either liquid or solid supported form, e.g., sulfuric acid, phosphoric acid, hydrofluoric acid, and aluminum chloride. Solid granular catalysts such as clays, zeolites, and amorphous materials have also been utilized in alkylation catalysts. A transalkylation reaction zone may be added to an alkylation zone to enable higher alkylation conversion through reaction of the resulting undesired polyalkylaromatics into desired monoalkylaromatic compounds. The transalkylation catalyst may be the same or a different composition than the alkylation catalyst. The alkylation may be effected in a variety of processing schemes employing one or more of an alkylation reaction zone, a transalkylation reaction zone, and a separations zone, with various product, feed, and intermediate-product recycles known to produce monoalkylaromatic products in high yields.

A drawback inherent to some alkylation/transalkylation processes using Friedel-Crafts catalysts such as solid phosphoric acid or hydrofluoric acid catalysts results from a water cofeed and resulting production of an extremely corrosive sludge by-product. The utilization of such sludge-producing catalysts in an alkylation process requires that costly special design provisions be made regarding unit metallurgy, safety, and by-product neutralization. The use of Friedel-Crafts catalysts additionally dictates a once-through processing scheme to ensure that damaging corrosive materials are not recycled into the reaction zone, necessitating operation of the process at high conversion with resulting greater amounts of unwanted byproducts such as alkylating agent oligomers and heavy alkylate.

Problems relating to the Friedel-Crafts catalysts were addressed by development of catalysts containing a zeolitic molecular sieve for the alkylation of aromatics, for example as disclosed in U.S. Pat. No. 3,751,504 (Keown et al.). Incorporation of magnesium into a zeolite for disproportionation of aromatics is disclosed in U.S. Pat. No. 4,034,053 (Kaeding et al.). Alkylation of an aromatic and an olefin using a crystalline magnesium silicate catalyst in which the magnesium is incorporated into the crystalline structure during its formation is disclosed in U.S. Pat. No. 4,721,827 (Cullo et al.). The use of a catalyst containing a MgAPSO non-zeolitic molecular sieve in hydrocarbon conversion including alkylation is disclosed in the aforementioned U.S. Pat. No. 4,758,419 (Lok et al.).

An ongoing issue facing workers in the aromatic-olefin alkylation field is how to reduce such process by-products such as olefin oligomers, heavy polyaromatic compounds, and unwanted monoalkylaromatics. Olefin oligomers are troublesome in that they often are recovered with the desired monoalkylaromatic product where they can detrimentally affect the utility of this intermediate in further conversion processes. An example of this would be the contamination of cumene with propylene oligomers which may reduce the utility of such contaminated cumene as a phenol process feedstock and ultimately for the production of phenolic resins due to the presence of the oligomers as an inert compound within the cross-linked resins. An example of unwanted monoaromatics is n-propyl benzene in cumene production, which is poorly converted in the phenol process and results in a yield loss through cumene purge and contamination of the acetone by-product with impurities.

SUMMARY OF THE INVENTION

A principal object of the present invention is to provide a novel molecular sieve which is useful for the conversion of hydrocarbons. More specifically, this invention is directed to a catalytic composition comprising a novel molecular sieve and a process for the alkylation of aromatics and olefins with improved yields and/or reduced processing costs.

This invention is based on the discovery that a MgAPSO molecular sieve having a framework magnesium content controlled within critical limits demonstrates a "volcano" effect in hydrocarbon-conversion activity.

Accordingly, a broad embodiment of the invention is directed toward a MgAPSO molecular sieve having a framework content of magnesium within a critical range. Preferably the sieve is incorporated into a catalytic composition having the substantial absence of a hydrogenation metal. The optimal catalytic composition comprises an inorganic-oxide matrix.

Another embodiment is directed toward a process for hydrocarbon conversion using a catalytic composition containing a MgAPSO molecular sieve having a content of magnesium within a critical range. Preferably the process comprises alkylation of a single-ring aromatic with an olefin to obtain primarily a monoalkylaromatic product. An especially preferred embodiment is the alkylation of benzene and propylene to obtain cumene, with an alternative being the alkylation of benzene and ethylene to obtain ethylbenzene. Optionally, polyalkylbenzene byproducts of the alkylation step are transalkylated to yield the desired monoalkylbenzene product.

These as well as other objects and embodiments will become evident from the following detailed description of the invention.

DETAILED DESCRIPTION OF THE INVENTION

Figure 1:
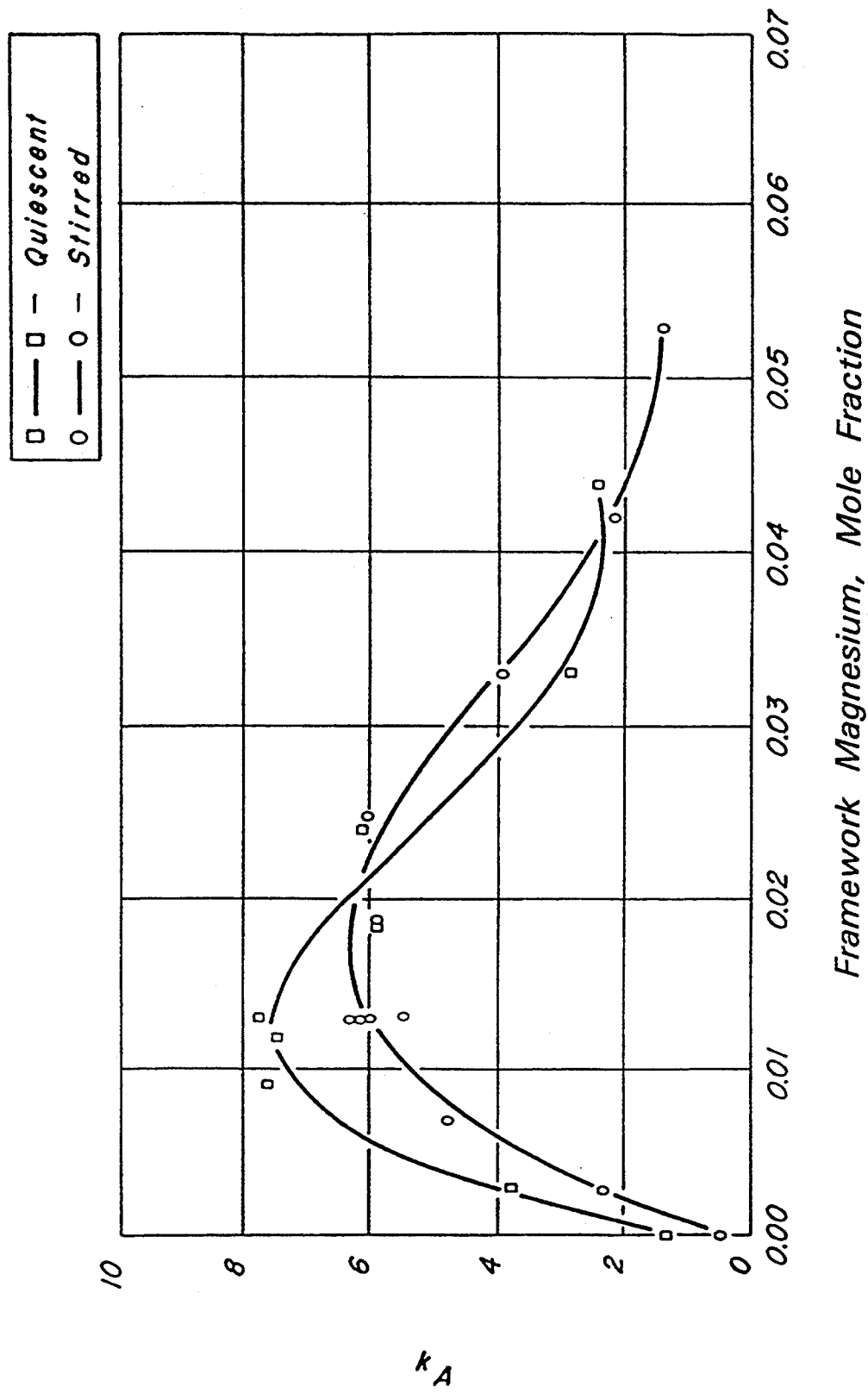
FIG. 1 compares the activity $k_A$ of MgAPSO molecular sieves having a range of framework magnesium contents.

As mentioned above, this invention is drawn to a MgAPSO molecular sieve having a framework content of magnesium within a critical range.

The MgAPSO molecular sieve of the invention can be understood by reference to the disclosure of U.S. Pat. No. 4,758,419, incorporated herein by reference thereto. MgAPSO sieves have a microporous crystalline framework structure of $MgO_2^{-2}$, $AlO_2^-$, $PO_2^+$, and $SiO_2$ tetrahedral units having an empirical chemical composition on an anhydrous basis expressed by the formula:

mR: $(Mg_wAl_xP_ySi_z)O_2$ wherein "R" represents at least one organic templating agent present in the intracrystalline pore system; "m" represents the molar amount of "R" present per mole of $(Mg_wAl_xP_ySi_z)O_2$ and has a value of zero to about 0.3; and "w", "x", "y" and "z" represent the mole fractions of element magnesium, aluminum, phosphorus and silicon, respectively, present as tetrahedral oxides. The mole fraction of each framework constituent of the molecular sieve is defined as a compositional value which is plotted in phase diagrams of U.S. Pat. No. 4,758,419. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

It is an essential aspect of the present invention that the magnesium content of the MgAPSO sieve is controlled within narrow limits. Specifically, the mol fraction "w" of framework magnesium in the molecular sieves of the invention is between about 0.003 and 0.035. Best results are obtained when the mol fraction of framework magnesium is between about 0.005 and 0.025.

A "volcano" effect has been observed on butane-cracking activity "$k_A$" when the magnesium content of the sieves is controlled within the above limits according to the invention. Volcano effect refers to an unusual and surprising increase in $k_A$ for sieves of the invention relative to sieves having both higher and lower magnesium contents. Butane-cracking activity is a readily determined representation of hydrocarbon-conversion activity in such processing areas as isomerization, reforming, dehydrocyclization, dehydrogenation, disproportionation, transalkylation, dealkylation, alkylation, polymerization, and catalytic cracking.

The butane cracking activity $k_A$ is determined by testing an 0.5 to 5-gram sample of 20–40 mesh MgAPSO sieve particles loaded into a cylindrical quartz tube, as described more specifically hereinafter in Example II. The quantity of sieves is selected to effect butane conversion of from 5% to 90% when butane is present in a concentration of 2 mole % in a helium carrier. The feedstock and reactor effluent are analyzed by conventional gas chromatography, and the pseudo-first-order rate constant $k_A$ is calculated from the analytical data.

The nomenclature employed herein to refer to the members of the class of MgAPSOs is consistent with that employed in the aforementioned patents. A particular member of a class is generally referred to as a "-n" species wherein "n" is an integer, e.g., MgAPSO-11, MgAPSO-31 and MgAPSO-41. The especially preferred species of the present invention is MgAPSO-31 having a characteristic X-ray powder diffraction pattern which contains at least the d-spacings set forth below:

| $2\theta$ | d | Relative Intensity |
|---|---|---|
| 8.4–9.501 | 10.53–9.3084 | w–s |
| 20.2–20.4 | 4.40–4.35 | m |
| 22.0–22.1 | 4.04–4.022 | m |
| 22.5–22.7 | 3.952–3.92 | vs |
| 23.15–23.35 | 2.831–2.814 | w–m |

MgAPSO sieves generally are synthesized by hydrothermal crystallization from an aqueous reaction mixture containing reactive sources of magnesium, silicon, aluminum and phosphorus and an organic templating agent for an effective time at effective conditions of pressure and temperature. The reaction-mixture compositions preferably are expressed in terms of molar ratios as follows:

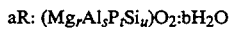

$$aR: (Mg_rAl_sP_tSi_u)O_2:bH_2O$$

wherein $(r+s+t+u)=1.00$ mole such that the aforementioned framework constituents "w", "x", "y" and "z" of the molecular sieves have the compositional values as described, the amount of organic templating agent "a" has a preferably positive value between 0 and about 6, and the amount of water "b" is between 0 and 500 with a preferable value between 2 and 300.

The organic templating agent, if any, can be selected from among those disclosed in U.S. Pat. No. 4,758,419. Generally this agent will contain one or more elements selected from Group VA (IUPAC 15) of the Periodic Table [See Cotton and Wilkinson, *Advanced Inorganic Chemistry*, John Wiley & Sons (Fifth Edition, 1988)], preferably nitrogen or phosphorus and especially nitrogen, and at least one alkyl or aryl group having from 1 to 8 carbon atoms. Preferred compounds include the amines and the quaternary phosphonium and quaternary ammonium compounds. Mono-, di- and tri-amines are advantageously utilized, either alone or in combination with a quaternary ammonium compound. Especially preferred amines include di-isopropylamine, di-n-propylamine, triethylamine and ethylbutylamine.

The reaction source of silicon may be silica, either as a silica sol or as fumed silica, a reactive solid amorphous precipitated silica, silica gel, alkoxides of silicon, silicic acid or alkali metal silicate and mixtures thereof.

The most suitable reactive source of phosphorus yet found for the instant process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds selected as templating agents do not, apparently, serve as reactive sources of phosphorus, but these compounds may be transformed in situ to a reactive source of phosphorus under suitable process conditions.

The preferred aluminum source is either an aluminum alkoxide, such as aluminum isopropoxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive source of magnesium can be introduced into the reaction system in any form which permits the formation in situ of a reactive form of magnesium, i.e., reactive to form the framework tetrahedral unit $MgO_2^{-2}$. Compounds of magnesium which may be employed include oxides, hydroxides, alkoxides, nitrates, sulfates, halides, carboxylates (e.g. acetates and the like), organo-metallics and mixtures thereof.

Crystallization generally is effected in a sealed pressure vessel, preferably lined with an inert plastic material such as polytetrafluoroethylene. While not essential in general to the synthesis of MgAPSO compositions, stirring or other moderate agitation of the reaction mixture and/or seeding the reaction mixture with seed crystals of either the MgAPSO species to be produced or a topologically similar aluminophosphate, alumino-silicate or other molecular sieve composition facilitates the crystallization procedure. The reaction mixture is maintained advantageously under autogenous pressure at a temperature between 50° and 250°, and preferably between 100° and 200° C., for a period of several hours to several weeks. The crystallization period advantageously will be between about 4 hours and 20 days. The MgAPSO product is recovered by any convenient method such as centrifugation or filtration.

Preferably the MgAPSO product comprises small crystallites, which favor high ethylbenzene conversion in a process isomerizing $C_8$ aromatics as demonstrated in the examples. Preferably the crystallites have a diameter, measured as the largest dimension across the crystallite, of not more than about 1.5 microns. There is little benefit and considerable effort in reducing crystallite size below about 0.5 micron, i.e., preferred crystallite size is from about 0.5 to 1.5 micron. More preferably, the crystallite size is at least about 0.75 micron. It is believed that the criticality of crystallite size relates to the conversion of ethylbenzene in such an isomerization process being diffusion-limited rather than surface-reaction limited, although such theory in not intended in any way to limit the invention.

The critical dimensions of the crystallites of the invention may be realized in any manner which is effective to reduce and control crystallite size. Larger crystallites may be milled to obtain smaller sizes, although this method is not preferred due to the range of sizes effected and possible structural damage. Preferable methods include high-speed stirring during crystallization to achieve high mass-transfer rates, higher solids in the reaction mixture, and use of suitable templates.

After crystallization the MgAPSO product may be isolated and advantageously washed with water and dried in air. The as-synthesized MgAPSO will typically contain within its internal pore system at least one form of any templating agent, also referred to herein as the "organic moiety", employed in its formation. Most commonly the organic moiety is present, at least in part, as a charge-balancing cation. In some cases, the MgAPSO pores are sufficiently large and the organic molecule sufficiently small that the removal of the latter may be effected by conventional desorption procedures. Generally, however, the organic moiety is an occluded molecular species which is too large to move freely through the pore system of the MgAPSO product and must be thermally degraded and removed by calcining at temperatures of from 200° to 700° C.

The MgAPSO compositions are formed from $MgO_2$, $AlO_2$, $PO_2$ and $SiO_2$ tetrahedral units which, respectively, have a net charge of $-2$, $-1$, $+1$ and 0. An $AlO_2^-$ tetrahedron can be balanced electrically either by association with a $PO_2^+$ tetrahedron or a simple cation such as an alkali metal cation, a proton ($H^+$), a cation of magnesium present in the reaction mixture, or an organic cation derived from the templating agent. Similarly, an $MgO_2^{-2}$ tetrahedron can be balanced electrically by association with $PO_2^+$ tetrahedra, a simple cation such as alkali metal cation, a proton ($H^+$), a cation of the magnesium, organic cations derived from the templating agent, or other divalent or polyvalent metal cations introduced from an extraneous source. Ion exchange of MgAPSO compositions will ordinarily be possible only after the organic moiety present as a result of synthesis has been removed from the pore system.

It is within the scope of the invention that a catalytic composition prepared from the MgAPSO of the invention comprises one or more additional non-zeolitic molecular sieves. Preferably the non-zeolitic molecular sieves are as a multi-compositional, multi-phase composite having contiguous phases, a common crystalline framework structure and exhibiting a distinct heterogeneity in composition, especially wherein one phase comprises a deposition substrate upon which another phase is deposited as an outer layer. Such composites are described in U.S. Pat. No. 4,861,739, incorporated herein by reference thereto. Suitable non-zeolitic molecular sieves include but are not limited to those of U.S. Pat. Nos. 4,440,871, 4,567,029 and 4,793,984, incorporated by reference. In a highly preferred embodiment the layered catalytic composition comprises a crystalline aluminophosphate of U.S. Pat. No. 4,310,440, incorporated by reference. The AlPO$_4$ of this embodiment is a crystalline metallophosphate whose essential framework structure has a chemical composition, expressed in terms of molar ratios of oxides, of:

$$Al_2O_3:1.0\pm0.2P_2O_5$$

AlPO$_4$-31 is especially preferred as a substrate and a MgAPSO, especially MgAPSO-31, as an outer layer.

A catalytic composition preferably is prepared by combining the molecular sieves of the invention with a binder for convenient formation of catalyst particles. The binder should be porous, adsorptive support having a surface area of about 25 to about 500 m$^2$/g, uniform in composition and relatively refractory to the conditions utilized in the hydrocarbon conversion process. The term "uniform in composition" denotes a support which is unlayered, has no concentration gradients of the species inherent to its composition, and is completely homogeneous in composition. Thus, if the support is a mixture of two or more refractory materials, the relative amounts of these materials will be constant and uniform throughout the entire support., It is intended to include within the scope of the present invention carrier materials which have traditionally been utilized in hydrocarbon conversion catalysts such as: (1) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as MgAl$_2$O$_4$, FeAl$_2$O$_4$, ZnAl$_2$O$_4$, CaAl$_2$O$_4$, and other like compounds having the formula MO-Al$_2$O$_3$ where M is a metal having a valence of 2; and (6) combinations of materials from one or more of these groups.

The preferred matrices for use in the present invention are refractory inorganic oxides, with best results obtained with a binder comprising alumina. Suitable aluminas are the crystalline aluminas known as the gamma-, eta-, and theta-aluminas. Excellent results are obtained with a matrix of substantially pure gamma-alumina. In addition, in some embodiments, the alumina matrix may contain minor proportions of other well known refractory inorganic oxides such as silica, zirconia, magnesia, etc. Whichever type of matrix is employed, it may be activated prior to use by one or more treatments including but not limited to drying, calcination, and steaming.

Using techniques commonly known to those skilled in the art, the catalytic composition of the instant invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing.

A preferred shape for the catalyst composite is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

An alternative shape of the composite is a sphere, continuously manufactured by the well-known oil drop method. Preferably, this method involves dropping the mixture of molecular sieve, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50°–200° C. and subjected to a calcination procedure at a temperature of about 450°–700° C. for a period of about 1 to about 20 hours. This treatment effects conversion of the hydrogel to the corresponding alumina matrix.

Preferably the catalytic composition is substantially free of a hydrogenation promoter which would result in economically significant losses of olefins by hydrogenation. The catalyst thus would contain less than 100 mass parts per million (ppm), on an elemental basis, of a hydrogenation promoter, and preferably less than about 10 mass ppm. "Hydrogenation promoter" usually comprises one or more of the Group VIII (8-10) metals nickel, cobalt, iron, and platinum-group metals platinum, palladium, rhodium, ruthenium, osmium, and iridium. The catalyst may contain trace amounts, within the above 100-ppm limit, of one or more platinum-group metals which could mitigate catalyst coking and deactivation in the presence of small amounts of hydrogen.

It is within the scope of the present invention that the catalytic composition may contain other metal components known to modify catalytic effects. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art.

The catalytic composition of the present invention may contain a halogen component. The halogen component may be either fluorine, chlorine, bromine or iodine or mixtures thereof. Chlorine is the preferred halogen component. The halogen component is generally present in a combined state with the inorganic-oxide support. The halogen component is preferably well dispersed throughout the catalyst and may comprise from more than 0.2 to about 15 wt. %, calculated on an elemental basis, of the final catalyst.

The halogen component may be incorporated in the catalytic composition in any suitable manner, either during the preparation of the inorganic-oxide support or before, while or after other catalytic components are incorporated. For example, the carrier material may contain halogen and thus contribute at least some portion of the halogen content in the final catalyst. The halogen component or a portion thereof also may be added to the catalyst during the incorporation of other catalyst components into the support, for example, by using chloroplatinic acid in impregnating a platinum component. Also, the halogen component or a portion thereof may be added to the catalyst by contacting with the halogen or a compound, solution, suspension or dispersion containing the halogen before or after other catalyst components are incorporated into the support.

The catalyst composite is dried at a temperature of from about 100° to about 320° C. for a period of from about 2 to about 24 or more hours and calcined at a temperature of from 400° to about 650° C. in an air atmosphere for a period of from about 0.1 to about 10 hours until the metallic compounds present are converted substantially to the oxide form. The optional halogen component may be adjusted by including a halogen or halogen-containing compound in the air atmosphere.

The resultant calcined composite may be subjected to a substantially water-free reduction step. Preferably, substantially pure and dry hydrogen (i.e., less than 20 vol. ppm $H_2O$) is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state.

The resulting reduced catalytic composite may, in some cases, be beneficially subjected to a presulfiding operation designed to incorporate in the catalytic composite from about 0.05 to about 0.5 mass % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 593° C. or more. It is generally a good practice to perform this presulfiding step operation under substantially water-free conditions.

MgAPSO sieves of the invention are useful for the conversion of hydrocarbons to obtain a converted product. The sieves preferably are utilized in combination with at least one inorganic-oxide matrix and one or more metals as described herein. A hydrocarbon feedstock is converted at hydrocarbon-conversion conditions including a pressure of about atmospheric to 200 atmospheres, temperatures of about 50° to 600° C., liquid hourly space velocities of from about 0.1 to 100 $hr^{-1}$, and, if hydrogen is present, hydrogen-to-hydrocarbon molar ratios of from about 0.1 to 80.

Hydrocarbon-conversion processes which could advantageously employ catalytic compositions containing the MgAPSO sieves of the invention include isomerization, reforming, dehydrocyclization, dehydrogenation, disproportionation, transalkylation, dealkylation, alkylation, polymerization, hydrocracking and catalytic cracking.

MgAPSO catalyst compositions used in reforming processes preferably contain a hydrogenation promoter such as a platinum-group metal, optionally one or more modifiers such as rhenium and Group IVA (14) metals, and an inorganic-oxide binder. Hydrocarbon feedstocks, preferably naphtha, contact the catalyst at pressures of between atmospheric and 40 atmospheres, temperatures of about 350° to 600° C., liquid hourly space velocities (LHSV) from 0.2 to 20 $hr^{-1}$, and hydrogen-to-hydrocarbon molar ratios of from about 0.1 to 10. Dehydrocyclization of naphthas and other paraffin-containing stocks is carried out over a similar catalyst, preferably nonacidic through incorporation of an alkali or alkaline earth metal, at similar conditions with operating pressure no higher than about 15 atmospheres. Products of reforming and dehydrocyclization generally have an increased concentration of aromatics relative to the feedstocks.

Isomerization of light hydrocarbons is advantageously effected using MgAPSO catalyst compositions within the scope of those described for use in reforming processes. The light hydrocarbon feedstock contacts the catalyst at pressures of between atmospheric and 70 atmospheres, temperatures of about 50° to 300, LHSV from 0.2 to 5 $hr^{-1}$, and hydrogen-to-hydrocarbon molar ratios of from about 0.1 to 5. Isomerization of olefins such as butenes, pentenes and higher olefins is effected over a catalyst which preferably does not contain a substantial hydrogenation component, in order to avoid olefin hydrogenation, at somewhat higher temperatures of 200° to 600° C. and higher space velocities of 0.5 to 100 $hr^{-1}$. Usually isomerization yields a product having a greater concentration of branched hydrocarbons.

Heavier paraffins, waxy distillates and raffinates are isomerized to increase the branching of the hydrocarbons using essentially the same catalyst compositions as used in reforming. Operating conditions include pressures of between about 20 and 150 atmospheres, temperatures of about 200° to 450° C., LHSV from 0.2 to 10 $hr^{-1}$, and hydrogen-to-hydrocarbon molar ratios of from about 0.5 to 10.

MgAPSO catalyst compositions used in hydrocracking processes preferably contain a hydrogenation promoter such as one or more of Group VIII (8–10) and Group VIB (6) metals and an inorganic-oxide matrix. A variety of feedstocks including atmospheric and vacuum distillates, cycle stocks and residues are cracked to yield lighter products at pressures of between 30 and 200 atmospheres, temperatures of about 200° to 450° C., LHSV from 0.1 to 10 hr$^{-1}$, and hydrogen-to-hydrocarbon molar ratios of from about 2 to 80.

Catalyst compositions of the same general description as those used in hydrocracking processes are useful in hydrotreating and hydrofining. A variety of naphthas, atmospheric and vacuum distillates, cracked and cycle stocks and residues are treated to remove sulfur, nitrogen and other heteroatoms and to saturate unsaturates at pressures of between 30 and 150 atmospheres, temperatures of about 200° to 450° C., LHSV from 0.1 to 20 hr$^{-1}$, and hydrogen-to-hydrocarbon molar ratios of from about 2 to 20. Operating conditions vary with respect to the difficulty of heteroatom removal, usually relating to the size and aromaticity of the containing molecules, and the concentration particularly of nitrogen in the feedstock. Products meet environmental requirements, are not as corrosive or contaminating of downstream equipment, or effect less deactivation of catalysts in downstream-processing units relative to the feedstock.

Disproportionation also is effected with MgAPSO catalyst compositions as described above in relation to reforming processes; optionally, the catalyst also contains one or more Group VIA (6) metals. Suitable feedstocks include single-ring aromatics, naphthalenes and light olefins, and the reaction yields more valuable products of the same hydrocarbon specie. Isomerization and transalkylation also may occur at the operating conditions of between 10 and 70 atmospheres, temperatures of about 200° to 500° C., and LHSV from 0.1 to 10 hr$^{-1}$. Hydrogen is optionally present at a molar ratio to hydrocarbon of from about 0.1 to 10.

An advantageous use for the MgAPSO sieve of the invention is in the isomerization of isomerizable alkylaromatic hydrocarbons of the general formula $C_6H_{(6-n)}R_n$, where n is an integer from 1 to 5 and R is $CH_3$, $C_2H_5$, $C_3H_7$, or $C_4H_9$, in any combination and including all the isomers thereof to obtain more valuable isomers of the alkylaromatic. A $C_8$-aromatic mixture containing ethylbenzene and xylenes, for example, may be isomerized at a temperature ranging from about 0° to about 600° C., pressure of from about 1 to 100 atmospheres absolute, liquid hourly space velocity of from about 0.1 to 30 hr$^{-1}$, and hydrogen-to-hydrocarbon ratio of from about 0.5 to 25.

The MgAPSO sieve of the invention is used to particular advantage in the alkylation of an aromatic substrate with an alkylating agent. An admixture of an alkylating agent and an aromatic substrate are passed into an alkylation zone containing an alkylation catalyst.

The alkylating agent may be selected from a group of diverse materials including monoolefins, diolefins, polyolefins, acetylenic hydrocarbons, and also alkylhalides, alcohols, ethers, esters, the later including the alkylsulfates, alkylphosphates and various esters of carboxylic acids. An olefin feedstock is preferred, particularly one comprising monoolefins containing one double bond per molecule. Monoolefins which may be utilized as the olefin feedstock are either normally gaseous or normally liquid at standard conditions, and include ethylene, propylene, 1-butene, 2-butene, isobutylene, and one or mixtures of the higher-molecular-weight normally liquid olefins such as the various pentenes, hexenes, heptenes, octenes, nonenes, decenes and higher olefins. In one embodiment, one or a mixture of substantially linear olefins, usually substantially within the range of $C_{11}$ to $C_{15}$ and derived, e.g., from dehydrogenation of petroleum-derived n-paraffins or ethylene oligomerization, are alkylated with benzene to obtain linear alkylbenzene as intermediates in the preparation of surface-active agents. Other feedstocks include higher molecular weight liquid olefins such as various olefin polymers having from about 9 to about 18 carbon atoms per molecule including propylene trimer, propylene tetramer, propylene pentamer, etc., and cycloolefins such as cyclopentene, methylcyclopentene, cyclohexene, methylcyclohexene, etc. It is a preferred embodiment of the present invention that the monoolefin contains at least 2 and not more than about 20 carbon atoms. It is especially preferred that the monoolefin be selected from one or both of ethylene and propylene.

The aromatic substrate of the present invention which is charged to the alkylation zone in admixture with the alkylating agent may be selected from a group of aromatic compounds which include one or a mixture of benzene, monocyclic alkyl-substituted benzenes of from 7 to 11 carbon atoms, and more highly condensed aromatics such as naphthalene, anthracene, phenanthrene, and biphenyl. Benzene or alkylbenzenes in which the alkyl groups comprise methyl, ethyl or a combination thereof are favored, such that the aromatic substrate portion of the feedstock may be benzene, benzene containing from 1 to 5 methyl and/or ethyl group substituents, and mixtures thereof. It is particularly preferred that the aromatic substrate comprises one or both of benzene and toluene, and especially that the aromatic substrate consists essentially of benzene. Cumene and ethylbenzene thus are especially preferred monoalkylaromatic products of the present invention.

In a continuous process for alkylating aromatic hydrocarbons with olefins, the previously described reactants are continuously fed into a pressure vessel containing the MgAPSO catalyst of the invention. The feed admixture may be introduced into the alkylation zone containing the alkylation catalyst at a constant rate, or alternatively, at a variable rate. Normally, the aromatic substrate and olefinic alkylating agent are contacted at a molar ratio of from about 1:1 to 20:1 and preferably from about 2:1 to 8:1. The preferred molar feed ratios help to maximize the catalyst life cycle by minimizing the deactivation of the catalyst by coke and heavy hydrocarbon deposition upon the catalyst.

The catalyst may be contained in one bed within a reactor vessel or divided up among a plurality of beds within a reactor. The alkylation reaction system may contain one or more reaction vessels in series. Reactants in the reactor vessel can flow vertically upwards, or downwards through the catalyst bed in a typical plug flow reactor, or horizontally across the catalyst bed in a radial flow type reactor.

In some cases, in order to maintain the reaction temperature in the preferred range and thus reduce the formation of unwanted polyalkylaromatics, it may be desirable to quench the reactants to dissipate heat of reaction. A quench stream comprised of the olefin alkylating agent, or a portion of the alkylation reactor effluent or mixtures thereof may be injected into the alkylation reactor system in order to dissipate heat and supply additional amounts of olefin alkylating agent and unreacted aromatic substrate at various locations within the reaction zone. This is accomplished for example in a single-stage reactor by multiple injection of the aforementioned quench steam components into the reaction zone via strategically placed inlet lines leading into said reaction zone. The amount and composition of quench material injected into either a single stage reaction system or multi-stage reaction system may be varied according to need. Benefits resulting from multiple quench injection include elimination of costly cooling apparatus in the process, provision for a larger heat sink and optimization of the olefin to aromatic compound molar ratio throughout the reaction zone thus resulting in improved selectivity to the desired monoalkylaromatic product. Additionally, multiple injection of quench material improves catalyst life.

Temperatures which are suitable for use in the process herein are those temperatures which initiate a reaction between an aromatic substrate and the particular olefin used to selectively produce the desired monoalkylaromatic compound. Temperatures suitable for use are from about 40° C. to about 400° C., optimally from about 100° C. to about 300° C.; lower temperatures in the range of about 100° C. to 275° C. are more suitable for alkylation of propylene and benzene, while temperatures of about 150° C. to 350° C. are preferred for ethylene-benzene alkylation. Pressures which are suitable for use herein preferably are those sufficient to maintain the reactants in the liquid phase at the operating temperature, generally at least about 100 kPa but usually not in excess of about 13 MPa. An especially desirable pressure range is from about 1 to about 4 MPa. Liquid hourly space velocity (LHSV) based upon the benzene feed rate suitably ranges from about 0.5 to about 50 $hr^{-1}$, and especially from about 2 to about 10 $hr^{-1}$.

By maintaining a liquid-phase process for producing alkylaromatics, the catalyst is continuously washed with reactants and buildup of coke precursors on the catalyst is mitigated or avoided. This results in reduced amounts of carbon forming on said catalyst in which case catalyst cycle life is extended as compared to a gas phase alkylation process in which coke formation and catalyst deactivation is a major problem. It is contemplated that $H_2$ may be added to the alkylation zone feed and the transalkylation zone feed in an amount, effecting a molar ratio to the aromatic substrate in the feed of at least about 0.01, sufficient to saturate highly reactive species in the alkylation-zone liquid feeds. The addition of $H_2$ in equilibrium amounts to the respective liquid phase feed streams helps to reduce the catalyst deactivation rate by inhibiting the polymerization potential of pore-blocking polymerizable compounds.

In some instances it may be desirable to depart from the preferred liquid-phase alkylation by employing catalytic distillation technology. The conditions employed in an alkylation zone within a catalytic distillation column will include mixed-phase conditions and may be dictated more by vapor-liquid equilibrium than reaction kinetic concerns. The catalyst may be retained within a structured packing such as shown in U.S. Pat. No. 5,073,236. Catalytic distillation would eliminate the need for separate alkylation and product-fractionation equipment if the required fractionation can be adequately performed in a catalytic distillation environment. The fractionation performed in the catalytic distillation column could separate out heavy hydrocarbons not intended as alkylation zone feed while also separating out the alkylation products. The alkylation of aromatic hydrocarbons via catalytic distillation is described in U.S. Pat. Nos. 5,043,506; 5,055,627; 5,080,871 and 5,118,896.

A substantial portion of the aromatic substrate and of the preferred olefin feedstock react in the alkylation zone in the presence of the MgAPSO alkylation catalyst to form, in addition to the desired monoalkylaromatic compound, polyalkylaromatic compounds. The polyalkylaromatic hydrocarbons may contain two or more alkyl groups, e.g., di- and triisopropylbenzene are byproducts of cumene production and di- and triethylbenzene are byproducts of ethylbenzene production. Although some of the polyalkylaromatic compounds may have industrial uses, they generally are produced in substantial excess to such uses in aromatic-olefin alkylation. Therefore, an optional aspect of the present invention is the recovery and transalkylation of these polyalkylaromatic compounds in order to maximize the amount of the desired monoalkylaromatic hydrocarbons such as cumene and ethylbenzene produced by the process.

Feed to the optional transalkylation zone comprises part or all of the polyalkylaromatic compounds and a suitable amount of aromatic substrate fraction to effect transalkylation. Usually the aromatic substrate feed to transalkylation is recovered from the hereinafter-described separation zone. Polyalkylaromatics and/or aromatic substrate originating from a source outside of the alkylation process optionally may be processed in the transalkylation zone. Transalkylation conditions and catalysts are within the parameters described hereinabove for the alkylation process, and the same catalyst optionally may be used for alkylation and transalkylation. Product from the transalkylation zone is directed, along with net alkylation-zone product, to the separation zone.

The alkylation-zone product may be divided into two portions, a recycle portion and a net portion. The net portion of the alkylation zone product suitably is directed to the separations zone, optionally along with transalkylation-zone product. The recycle portion optionally is recycled to the inlet of the alkylation reactor and admixed with the alkylating agent and aromatic substrate and/or used as all or a portion of a reaction zone quench stream as hereinbefore mentioned. The portion that is recycled to the inlet of the alkylation reactor comprises from 0 to 95 wt. %, and preferably 50 to 90 wt. %, of the alkylation-zone product. This recycle portion enables the alkylation process to be operated at a per-pass conversion rate that effects high monoalkylaromatic production concomitant with reasonably sized separation-zone equipment.

The net alkylation-zone product is separated into at least three fractions using any suitable separation techniques that will recover (1) unconverted aromatic substrate, (2) a monoalkylaromatic product, and (3) a polyalkylaromatic compound. An example of some of the separations techniques that could be employed alone or in combination in the separations zone to obtain these fractions are: distillation including vacuum, atmospheric, and superatmospheric distillation; extraction techniques including, for example, liquid/liquid extractions, vapor/liquid extractions, and supercritical extractions; absorption techniques, adsorption techniques, and any other known mass transfer techniques which can achieve the desired recovery and purity of the fractions. The separation-zone processing conditions depend upon the choice of the separation techniques employed; suitable embodiments are known in the art, not being a distinguishing feature of the present invention. Continuous distillation is the generally preferred technique used in the separation zone.

Part or all of the fresh aromatic-substrate feed stream may be directed to the separation zone. In this manner, deleterious components in this feed stream may be removed before the aromatic substrate is alkylated or converted by transalkylation. The recovered aromatic substrate from the separation zone thus may originate from both fresh feed and unconverted substrate from alkylation and transalkylation, and is returned as a substantially pure feed stream to the alkylation and optional transalkylation zones. Usually from about 25 wt. % to about 100 wt. %, and preferably from about 30 wt. % to about 85 wt. % of the aromatic substrate is directed to the alkylation zone. The remainder of the aromatic substrate and the entire polyalkylated aromatic fraction may be directed to the optional transalkylation zone as the transalkylation-zone feed.

The separation zone generally yields, along with monoalkylaromatic product and polyalkylaromatic stream, a byproduct comprising hydrocarbon materials lower in molecular weight than the aromatic substrate; this usually comprises light paraffins and unconverted olefins which may be processed in other units or may have only fuel value. A net product distilling above the polyalkylaromatics which is not suitable for transalkylation may be recovered from the separation zone as a fuel product. The desired monoalkylaromatic product generally is recovered having high purity, usually in excess of 95 mass %, preferably higher than about 99 mass %, and optimally about 99.9 mass % or higher.

EXAMPLES

The following examples are presented for purpose of illustration only and are not intended to limit the scope of the present invention. The examples demonstrate the criticality of magnesium content in molecular sieves of the invention by butane-cracking activity and demonstrate the utility of the catalyst for alkylation of aromatics and olefins.

MgAPSO-31 compositions have been prepared and tested employing reaction mixtures having a molar composition expressed as:

a R:rMgO:s Al$_2$O$_3$:tP$_2$O$_5$:u SiO$_2$:b H$_2$O:

wherein the values a, r, s, t, u and b represent moles of template R, magnesium (expressed as the oxide), Al$_2$O$_3$, P$_2$O$_5$ (H$_3$PO$_4$ expressed as P$_2$O$_5$), SiO$_2$ and H$_2$O, respectively. The values ranged as follows, based on t=1:

| a | 1.5–2.0 |
| r | as described hereinbelow |
| s | 0.75–1.1 |
| u | 0.1–1.2 (usually 0.6) |
| b | 40–80 |

These ranges do not, however, limit the applicability of the present invention as described hereinabove.

Example I

Tests are reported below for MgAPSO-31 compositions prepared via reaction mixtures having a molar composition of about:

1.5 R:rMgO:0.9 Al$_2$O$_3$:P$_2$O$_5$:0.3 SiO$_2$:50 H$_2$O:

The value r was varied to provide a range of mol fractions of framework magnesium in the context of the previously defined formula:

(Mg$_w$ Al$_x$ P$_y$ Si$_z$)

wherein (w+x+y+z)=1.00 and w is the mol fraction of framework magnesium.

The reaction mixture was prepared by mixing the Al$_2$O$_3$ as pseudoboehmite (Versal 250) into the H$_3$PO$_4$ and water on a gradual basis and blending until a homogeneous mixture was observed. Magnesium acetate was dissolved in a portion of the water and then was added followed by addition of LUDOX-LS. The combined mixture was blended until a homogeneous mixture was observed. The organic templating agent (ethylbutylamine) and AlPO$_4$-31 seed were added to this mixture and blended until a homogeneous mixture was observed. Portions of the resulting mixture were placed in either lined (polytetrafluoroethylene) stainless steel pressure vessels for quiescent crystallization or an unlined stirred stainless steel pressure vessel and heated up to about 200° C, to effect crystallization at autogenous pressure. The products were removed from the reaction vessel, cooled and evaluated as set forth hereinafter.

The examples present test results obtained when catalysts of the invention were evaluated in an isomerization process. The catalysts were evaluated using a pilot plant flow reactor processing a non-equilibrium C$_8$ aromatic feed comprising 52.0 mass % meta-xylene, 18.5 mass % ortho-xylene, 0.1 mass % para-xylene, 21.3 mass % ethylbenzene, and 0.1 mass % toluene, with the balance being nonaromatic hydrocarbons. This feed was contacted with 100 cc of catalyst at a liquid hourly space velocity of 2, and a hydrogen/hydrocarbon mole ratio of 4. Reactor pressure and temperature were adjusted to cover a range of conversion values in order to develop the relationship between C$_8$ ring loss and approach to xylene equilibrium (as determined by product para-xylene to total xylene mole ratio). At the same time, at each temperature, the pressure was chosen to maintain a constant mole ratio of C$_8$ naphthenes to C$_8$ aromatics of approximately 0.06.

Example II

A representation of the hydrocarbon-conversion activity of the present class of medium-pore molecular sieves is the butane-cracking activity "k$_A$" determined using a bench-scale apparatus. This activity measurement allows larger number of samples to be surveyed with more consistent results than, e.g., isomerization performance in a pilot plant. The reactor is a cylindrical quartz tube having a length of 254 mm and an I.D. of 10.3 mm. In each test the reactor was loaded with 20–40 mesh (U.S. std.) particles of the MgAPSO-31 molecular sieve in an amount of from 0.5 to 5 grams, the quantity being selected so that the conversion of n-butane was at least 5% and not more than 90% under the test conditions. As-synthesized samples containing organics are first calcined in situ in the reactor in air at 600° C., for one hour to remove organic materials from the pore system, then in a flowing stream of helium at 500° C. for at least 10 minutes. The activity k$_A$ then was determined using a feedstock consisting of a helium/n-butane mixture containing 2 mole percent n-butane which is passed through the reactor at a rate of 50 cc/minute. The feedstock and the reactor effluent were analyzed using conventional gas chromatography techniques, reactor effluent being analyzed after 10 minutes of on-stream operation at 500° C. The pseudo-first-order rate constant k$_A$ was calculated from the analytical data.

Eighteen samples of MgAPSO-31 with varying magnesium contents, and two controls without magnesium, were prepared according to the procedure of Example I. Crystallization was carried out at 200° C. with eight samples in a quiescent reaction mixture and ten stirred samples. The activity $k_A$ of the samples was determined according to the procedure described hereinabove and plotted in FIG. 1. The samples showed particularly high activities in the region of 0.005–0.025 mole fraction of magnesium, with some increased activity at 0.003 and 0.03–0.035 mole fraction magnesium and low activities at the outer limits of the tests. Activities of the eleven most active samples in the middle of the range were twice or three times those of samples containing the highest concentrations of framework magnesium.

Example III

Figure 2:
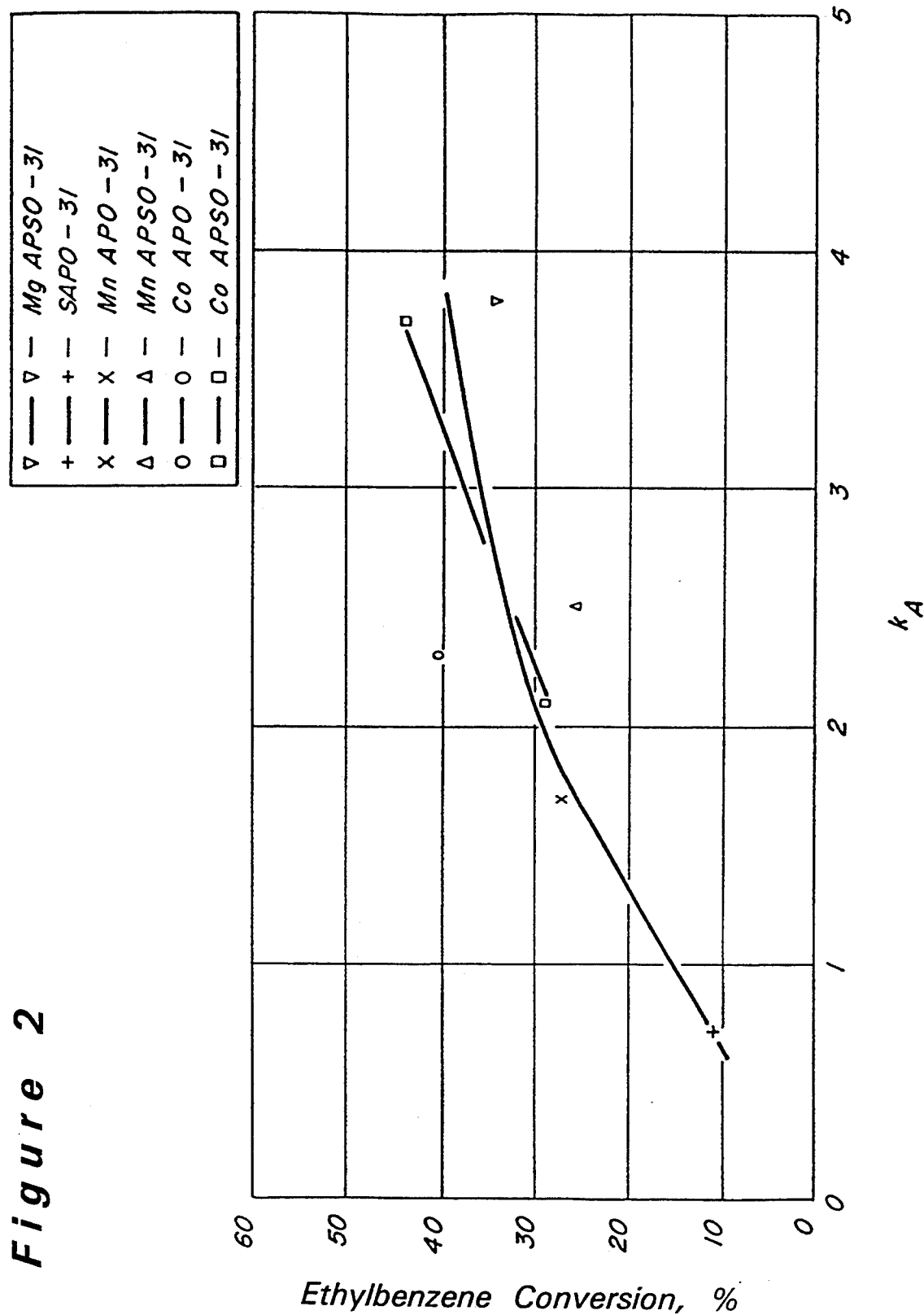
FIG. 2 relates $k_A$ and ethylbenzene conversion for several different molecular sieves.

Butane-cracking activity $k_A$ was related to ethylbenzene conversion. Seven non-zeolitic molecular-sieve samples were tested for ethylbenzene conversion at a pressure of 20 atmospheres, temperature of 427° C., and mass hourly space velocity of 4 using a feed of 17 mass % ethylbenzene and 83 mass % meta-xylene. Ethylbenzene ("EB") conversion was chosen as the measure of comparison since ethylbenzene is the most difficult of the $C_8$-aromatics isomers to convert in an isomerization process. The activity $k_A$ also was determined for the seven samples in accordance with the procedure of Example II. Results were as follows, and also are plotted in FIG. 2:

| Catalyst | EB Conversion, % | $k_A$ |
| --- | --- | --- |
| SAPO-31 | 11 | 0.7 |
| MgAPSO-31 | 34 | 3.8 |
| MnAPSO-31 | 25 | 2.4 |
| MnAPO-31 | 28 | 1.7 |
| CoAPO-31 | 41 | 2.3 |
| CoAPSO-31 | 29 | 2.1 |
| CoAPSO-31 | 44 | 3.7 |

There is a clear correlation between $k_A$ and ethylbenzene conversion, even though there is some scatter in the data points as would be expected from the testing of a variety of molecular sieves.

Example IV

The utility of a catalytic composition of the present invention for benzene alkylation with propylene to form cumene was demonstrated. The catalyst contained 35 mass % of MgAPSO-31, containing 0.01 mol fraction magnesium, and 65 mass % alumina.

The feedstock consisted essentially of benzene and propylene in a molar ratio of 8.5:1, respectively. Operating temperature was raised to an average of 181° C. for a series of four tests. Propylene conversion averaged 84% for the tests with a maximum variance of less than 1%. Selectivities averaged as follows in mass %:

| Cumene | 80.87 |
| --- | --- |
| Diisopropylbenzene | 8.82 |
| Heavies | 8.35 |

The diisopropylbenzene and a portion of the heavies (triisopropylbenzene and heavier) could be recycled to yield additional cumene. The undesirable cumene contaminant n-propylbenzene could not be detected in the product at the ppm level.

Example V

The utility of a catalytic composition of the present invention for benzene alkylation with ethylene to form ethylbenzene was demonstrated. The catalyst was identical to that used in Example IV.

The feedstock consisted essentially of benzene and ethylene in a molar ratio of 11.5:1, respectively. Operating temperature was raised to an average of 252° C. for a series of four tests. Ethylene conversion averaged 63% for the tests with a maximum variance of less than 4%. Selectivities averaged as follows in mass %:

| Ethylbenzene | 82.96 |
| --- | --- |
| Di- + triethylbenzenes | 5.79 |
| Heavies | 10.77 |

The di- and triethylbenzenes and a portion of the heavies (tetraethylbenzene and heavier) could be recycled to yield additional ethylbenzene.

We claim:

1. An aromatic-olefin alkylation process which comprises contacting benzene with an olefin feedstock in an alkylation zone at alkylation conditions comprising a temperature of from about 40° to 400° C., a pressure of from about 100 kPa to 13 MPa, and a liquid hourly space velocity of from about 0.5 to 50 $hr^{-1}$ with catalytic composition comprising a MgAPSO molecular sieve, said sieve comprising from about 0.003 to 0.035 mol fraction of magnesium in the microporous crystalline framework structure, to obtain a monoalkylaromatic product.

2. The, process of claim 1 wherein the content of magnesium in the microporous crystalline framework structure of the sieve is from about 0.005 to 0.025 mol fraction.

3. The process of claim 1 wherein the MgAPSO comprises MgAPSO-31.

4. The process of claim 1 wherein the catalytic composition further comprises an inorganic-oxide matrix.

5. The process of claim 4 wherein the inorganic-oxide matrix comprises alumina.

6. The process of claim 1 wherein the catalytic composition is substantially free of a hydrogenation promoter.

7. The process of claim 1 wherein the alkylation is carried out in the liquid phase.

8. The process of claim 1 wherein free hydrogen is present in an amount of at least about 0.01 mols per mol of aromatic hydrocarbon.

9. The process of claim 1 wherein the olefin feedstock comprises propylene and the monoalkylaromatic product comprises cumene.

10. The process of claim 1 wherein the olefin feedstock comprises ethylene and the monoalkylaromatic product comprises ethylbenzene.

11. The process of claim 1 wherein the monoalkylaromatic product is recovered in a separation zone with a purity of at least about 99 mass %.

12. The process of claim 1 further comprising transalkylation of polyaromatic compounds formed in the alkylation zone in a transalkylation zone at transalkylation conditions with a transalkylation catalyst to obtain additional monoalkylaromatic product.

13. The process of claim 12 wherein the transalkylation catalyst comprises a MgAPSO molecular sieve, said sieve comprising from about 0.003 to 0.035 mol fraction of magnesium in the microporous crystalline framework structure.

14. A benzene-propylene alkylation process which comprises contacting benzene with a propylene feedstock, at alkylation conditions comprising a temperature of from about 100° to 275° C., a pressure of from about 100 kPa to 13 MPa, and a liquid hourly space velocity of from about 0.5 to 50 hr$^{-1}$, with a catalytic composition comprising a MgAPSO molecular sieve, said sieve comprising from about 0.003 to 0.035 mol fraction of magnesium in the microporous crystalline framework structure, to obtain a cumene product.

15. The process of claim 14 wherein the alkylation is carried out in the liquid phase.

16. The process of claim 14 wherein free hydrogen is present in an amount of at least about 0.01 mols per mol aromatic hydrocarbon.

17. A benzene-ethylene alkylation process which comprises contacting benzene with an ethylene feedstock, at alkylation conditions comprising a temperature of from about 150° to 350° C., a pressure of from about 100 kPa to 13 MPa, and a liquid hourly space velocity of from about 0.5 to 50 hr$^{-1}$, with a catalytic composition comprising a MgAPSO molecular sieve, said sieve comprising from about 0.003 to 0.035 mol fraction of magnesium in the microporous crystalline framework structure, to obtain an ethylbenzene product.

18. The process of claim 17 wherein the alkylation is carried out in the liquid phase.

19. The process of claim 17 wherein free hydrogen is present in an amount of at least about 0.01 mols per mol of aromatic hydrocarbon.

* * * * *